United States Patent [19]

Hechenbleikner et al.

[11] 4,450,113

[45] May 22, 1984

[54] ZEROVALENT NICKEL PHOSPHITE COMPLEXES

[75] Inventors: Ingenuin Hechenbleikner, West Cornwall; William P. Enlow, Falls Village, both of Conn.; David C. Lankin, Schaumburg, Ill.

[73] Assignee: Borg-Warner Chemicals, Inc., Parkersburg, W. Va.

[21] Appl. No.: 406,732

[22] Filed: Aug. 9, 1982

[51] Int. Cl.$^3$ .............................................. C07F 15/04
[52] U.S. Cl. ............................................... 260/439 R
[58] Field of Search ............................. 260/403, 439 R

[56] References Cited

U.S. PATENT DOCUMENTS

| | | | |
|---|---|---|---|
| 3,102,899 | 9/1963 | Cannell | 260/439 R |
| 3,152,158 | 10/1964 | Clark | 260/439 |
| 3,271,438 | 9/1966 | Cannell | 260/439 R X |
| 3,328,443 | 6/1967 | Clark et al. | 260/439 R |
| 3,346,608 | 10/1967 | von Kutepow et al. | 260/439 R |
| 3,661,843 | 5/1972 | Hechenbleikner et al. | 260/439 R X |
| 3,903,120 | 9/1975 | Shook | 260/439 R |
| 3,959,220 | 5/1976 | Hechenbleikner et al. | 260/439 CY X |
| 4,012,399 | 3/1977 | Hechenbleikner et al. | 260/439 R |
| 4,276,195 | 6/1981 | Verkade | 252/431 P |

*Primary Examiner*—Helen M. S. Sneed
*Attorney, Agent, or Firm*—Joseph Shekleton

[57] ABSTRACT

Organic zerovalent nickel complexes wherein the organic portion is derived from an ester of pentaerythritol phosphite. The complexes are believed to have a tetrahedral structure; one nickel atom is complexed with four molecules of the pentaerythritol phosphite ester. The nickel complexes are useful as polymer additives, being effective to impart improved resistance to deterioration of olefin polymers upon exposure to ultraviolet light.

6 Claims, No Drawings

ZEROVALENT NICKEL PHOSPHITE COMPLEXES

This invention relates as indicated to certain organic nickel complexes. More particularly it relates to such organic nickel complexes which are effective to impart to olefin polymer compositions an enhanced resistance to deterioration ordinarily resulting from exposure of such olefin polymer compositions to ultraviolet light.

BACKGROUND OF THE INVENTION

In general, nickel compounds exist as one of three geometric configurations, square planar, tetrahedral (where nickel has a coordination number of 4), or octahedral (where nickel has a coordination number of 6). The latter is the most common. The organic nickel complexes here are believed to have a tetrahedral structure inasmuch as they are derivable from nickel carbonyl which is known to have a tetrahedral structure.

Certain organic nickel complexes are known to be effective ultraviolet stabilizing agents because, it is believed, they tend to inactivate excited molecular species which otherwise would cause chain scission and degradation of the polymer molecule.

U.S. Pat. No. 3,661,843 (Hechenbleikner et al.), for example, shows the utilization as stabilizers of organic solid polymer materials of a wide variety of organic nickel complexes which contain phosphorus. One of the organic nickel complexes shown, at column 16, lines 8-13, is characterized by the structural formula

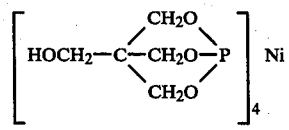

It apparently was prepared by the reaction of nickel carbonyl and pentaerythritol phosphite.

U.S. Pat. No. 3,959,220 (Hechenbleikner et al.) and U.S. Pat. No. 4,012,399 (Hechenbleikner et al.) have the same disclosure as that of the above Hechenbleikner et al. patent.

U.S. Pat. No. 4,276,195 shows the reaction of a normally homogenous transition metal catalyst, such as tetrakis trimethylphosphite nickel(0), with a polydentate ligand such as dimethyl pentaerythritol diphosphite. The product is a polymeric solid which is an effective catalyst in the isomerization of olefins.

SUMMARY OF THE INVENTION

The invention here is a zerovalent nickel complex having the structural formula

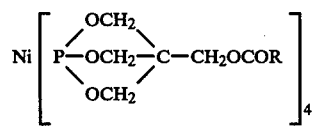

where R is alkyl of 1-18 carbon atoms, phenyl, alkylphenyl, hydroxyphenyl, or

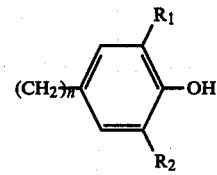

where $R_1$ and $R_2$ are lower alkyl, and n is 0-2.

DESCRIPTION OF THE PREFERRED EMBODIMENTS

The alkyl groups ($R_1$ and $R_2$) in the above structural formulas are lower alkyl groups. A "lower alkyl" group, for purposes of this invention, is one having 1-6 carbon atoms. Preferably, where attached to the phenolic ring above, these lower alkyl groups should be bulky groups, i.e., either secondary or tertiary alkyl groups such as isopropyl, sec-butyl, tertiarybutyl, n-amyl, tertiaryamyl, 2,2-dimethylbutyl and 2-methyl-2-ethylpropyl. Particularly preferred are those organic nickel complexes of these types where the alkyl groups are tertiarybutyl.

R as indicated may be an alkyl group of 1-18 carbon atoms. It may be either straight chain or branch chain. Methyl, ethyl, isopropyl, isobutyl, n-hexyl, n-octyl, n-decyl, isododecyl and octadecyl are illustrative. R may also be alkylphenyl in which case the alkyl group preferably contains 1-6 carbon atoms.

The organic nickel complexes of the invention are prepared by an exchange reaction between the nickel-trimethyl phosphite complex of the structure

and the appropriate pentaerythritol phosphite. The exchange reaction proceeds very simply, merely upon mixing the two reactants and heating the mixture, usually at reduced pressure to permit easy removal of displaced trimethyl phosphite by distillation. When no more trimethyl phosphite distills the reaction is finished. The residue is the product. It may be purified by washing with a solvent such as heptane or acetone. No catalyst is required; a solvent, e.g., chlorobenzene, o-dichlorobenzene, xylene and toluene, may be used. The temperature of the reaction may range from slightly above room temperature, e.g., 40° C., to as high as 150° C.

The nickel-trimethyl phosphite reactant may be prepared by mixing nickel chloride ($NiCl_2$) and trimethyl phosphite in the presence of an alkaline material such as sodium carbonate, and methanol. The reaction proceeds according to the following equation:

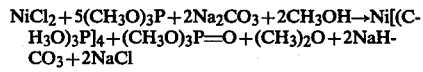

The nickel-trimethyl phosphite complex is a solid, crystallizable from hexane.

Olefin polymers that can be stabilized with compositions comprising a zerovalent nickel complex according to this invention include alpha olefin polymers such as polyethylene, polypropylene, polybutene, poly-3-methylbutene, or copolymers thereof such as ethylene vinyl acetate copolymer and ethylene propylene copolymer, polybutadiene, polyisoprene, polystyrene, poly(vinyl acetate), copolymers of styrene and another monomer (for example, maleic anhydride, butadiene, acrylonitrile, etc.), acrylonitrile-butadiene-styrene copolymer, acrylic acid ester-butadiene-styrene copolymer, methacrylic acid ester-butadiene-styrene copolymer, methacrylate ester resin such as poly(methylmethacrylate), poly(vinyl-alcohol), etc.

The following examples show the preparation of the nickel-trimethyl phosphite and its use in the preparation of the zerovalent nickel complexes of the invention.

EXAMPLE 1

To a stirred mixture of 310 g. (2.5 mol) of trimethyl phosphite, 106 g. (1.0 mol) of sodium carbonate and 200 ml. of methanol there is added portionwise, over a period of 90 minutes, a solution of 64.5 g. (0.50 mol) of nickel chloride in 200 ml. of methanol. A slightly exothermic reaction ensues causing the temperature to rise to 35° C. Stirring is continued until the mixture is colorless, whereupon the product mixture is heated at reflux temperature for two hours, then cooled and filtered. The filtrate is concentrated by evaporation at reduced pressure and the residue (tetrakis trimethyl phosphite nickel(0)) is crystallized from n-heptane. Yield: 80% of a colorless, crystalline solid; M.P., 115°–118° C.

EXAMPLE 2

A mixture of 7.2 g. (0.013 mol) of tetrakis trimethylphosphite nickel(0) and 22.9 g. (0.054 mol) of the ester of pentaerythritol phosphite and 3-(30′,5′-ditertiarybutyl-4′-hydroxyphenyl) propionic acid is heated with stirring, over a period of one hour, to 170° C./22 mm. During this period trimethyl phosphite is collected as a distillate. The green, glassy residue weighs 25.2 g., M.P., 85°–100° C.

EXAMPLE 3

A solution of 8.3 g. (0.015 mol) of tetrakis trimethyl phosphite nickel(0) and 24.4 g. (0.062 mol) of the ester of pentaerythritol phosphite and 3,5-ditertiarybutyl-4-hydroxybenzoic acid in 20 ml. of toluene is heated with stirring to 150° C./25 mm. The residue is crystallized from a 60/40 mixture of heptane and toluene. The yield of light yellow crystalline solid, M.P., 215°–220° C., is 20.6 g. (83.7% of the theory).

EXAMPLE 4

A mixture of 12.2 g. (0.022 mol) of tetrakis trimethyl phosphite nickel(0) and 24.4 g. (0.091 mol) of the ester of pentaerythritol phosphite and benzoic acid is heated with stirring to 150° C./22 mm. and held at these conditions for 45 minutes. The residue is washed with toluene, then freed of last traces of the toluene by heating to 80° C./20 mm. The yield of white solid is 21.3 g.

EXAMPLE 5

A mixture of 11.65 g. (0.021 mol) of tetrakis trimethyl phosphite nickel(0) and 25 g. (0.088 mol) of the ester of pentaerythritol phosphite and salicyclic acid is heated to 165° C./20 mm., then held at 100° C./20 mm. for 60 minutes. The residue is washed with toluene and dried. The yield of colorless solid is 23 g., M.P., 250° C. (with decomposition).

EXAMPLE 6

A mixture of 27.7 g. (0.05 mol) of tetrakis trimethyl phosphite nickel(0), 41.2 g. (0.20 mol) of the acetate of pentaerythritol phosphite and 200 ml. of o-dichlorobenzene is heated with stirring to 130° C./140 mm. A total of 30 ml. of distillate is collected. The residue is cooled, diluted with heptane, filtered, and the solid dried and washed with heptane and dried.

EXAMPLE 7

A mixture of 12.5 g. (0.023 mol) of tetrakis trimethyl phosphite nickel(0) and 30.1 g. (0.095 mol) of the n-decanoate of pentaerythritol phosphite is heated with stirring to 165° C./20 mm. The vacuum is broken with nitrogen. The residue in the reaction flask weighs 31.3 g. It is warmed in 70 ml. toluene to 70° C. and filtered. The cooled filtrate deposits crystals which are recrystallized from acetonitrile to yield 21.5 g. of a colorless solid, M.P., 245°–254° C. (dec.).

The efficacy of the organic nickel complexes of this invention as polymer stabilizers is shown by the test data set out in Table I. The data is obtained from atmospheric tests carried out in Puerto Rico. Test samples are in the form of 200/16 denier polypropylene multifilaments consisting of polypropylene, 0.05 phr (parts per hundred parts of resin) of calcium stearate, 0.15 phr of tris-(3,5-ditertiarybutyl-4-hydroxybenzyl) isocyanurate and the indicated amounts (as Ni) of nickel complex and 531, a known UV absorber commonly used to enhance the UV inhibiting activity of nickel compounds. The tensile strength of each sample is determined before the test is begun and at periodic intervals thereafter during exposure to the atmosphere. The degree of such exposure (in terms of kilolangleys) required to reduce the tensile strength to one half its original value is taken as the point of failure of the sample.

TABLE I

| | Kilolangleys of Exposure Required to Reach 50% of Original Tensile Strength | | | | | |
|---|---|---|---|---|---|---|
| | Amounts | | | | | |
| Ni Complex | 1 | 2 | 3 | 4 | 5 | 6 |
| 1084[a] | 0.5 | | | 0.25 | | |
| Product of Ex 6 | | 0.5 | | | 0.25 | |
| Product of Ex 2 | | | 0.5 | | | 0.25 |
| 531[b] | | | | 0.25 | 0.25 | 0.25 |
| Kilolangleys | 40 | 54 | 40 | 49 | 102 | 82 |

[a] 2,2′-thiobis-(4-tertiaryoctylphenolate)n-butylamine nickel II
[b] 4-Octoxy-2-hydroxybenzophenone Test sample 1084 is a well known and widely used nickel-containing ultraviolet light stabilizer.

Similar results, obtained from the same type of test, are shown in Table II where the test samples contain slightly less of the tris-(3,5-ditertiarybutyl-4-hydroxybenzyl) isocyanurate component, i.e., 0.10 phr. These test samples also contain 0.05 phr of calcium stearate plus the indicated amounts (as Ni) of nickel compounds.

TABLE II

| | Kilolangleys of Exposure Required to Reach 50% of Orginal Tensile Strength | | | | | |
|---|---|---|---|---|---|---|
| Test Sample | 1084 | 2002[c] | Prod. of Ex. 6 | Prod. of Ex. 2 | 531 | Kilolangleys |
| 1 | 0.25 | | | | | 51 |
| 2 | | 0.25 | | | | 58 |
| 3 | | | 0.25 | | | 66 |
| 4 | 0.50 | | | | | 36 |
| 5 | | 0.50 | | | | 56 |
| 6 | 0.25 | | | | 0.25 | 60 |
| 7 | | 0.25 | | | 0.25 | 84 |
| 8 | | | 0.25 | | 0.25 | >104 |

TABLE II-continued

| Test Sample | Kilolangleys of Exposure Required to Reach 50% of Orginal Tensile Strength | | | | | |
|---|---|---|---|---|---|---|
| | 1084 | 2002[c] | Prod. of Ex. 6 | Prod. of Ex. 2 | 531 | Kilolangleys |
| 9 | | | | 0.25 | 0.25 | 80 |

[c]Nickel ethyl(3,5-ditertiarybutyl-4-hydroxybenzyl)phosphonate

Decomposition of nickel-containing stabilizers at polypropylene processing temperatures is a common problem. The nickel complexes of this invention, when extruded and then subjected to severe molding conditions, cause less build-up in the feed section of the extruder screw than do 1084 and 2002, for example.

The zerovalent nickel complex of pentaerythritol phosphite, shown in U.S. Pat. No. 3,661,843 (Hechenbleikner et al.) is rated 60 in the above Exposure Test, when tested at a concentration of 0.50 phr (as Ni). This rating is comparable with that for Sample No. 3 in Table II which, it will be noted, is tested at a concentration of 0.25 phr (as Ni). That is, the zerovalent nickel complex of this invention is better than the zerovalent nickel complex of the prior art, even when tested at one half the concentration.

All parts and percentages herein, unless otherwise expressly stated, are by weight.

We claim:

1. A zerovalent nickel complex having the structural formula

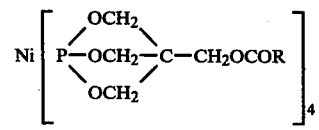

where R is alkyl of 1–18 carbon atoms, phenyl, alkylphenyl wherein the alkyl contains 1–6 carbon atoms, hydroxyphenyl or

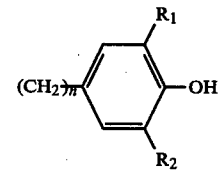

where $R_1$ and $R_2$ are lower alkyl, and n is 0–2.

2. The zerovalent nickel complex of claim 1 wherein R is methyl.

3. The zerovalent nickel complex of claim 1 wherein R is 2(3',5'-dialkyl-4'-hydroxyphenyl)ethyl.

4. The zerovalent nickel complex of claim 3 wherein $R_1$ and $R_2$ each are bulky groups.

5. The zerovalent nickel complex of claim 3 wherein the alkyl groups are tertiary alkyl groups.

6. The zerovalent nickel complex of claim 3 wherein the alkyl groups are tertiarybutyl groups.

* * * * *